(12) United States Patent
DeWolf et al.

(10) Patent No.: US 11,337,744 B1
(45) Date of Patent: May 24, 2022

(54) SYSTEM AND METHOD FOR SCAPHOID FIXATION

(71) Applicant: Dartmouth-Hitchcock Clinic, Lebanon, NH (US)

(72) Inventors: Matthew C. DeWolf, Lebanon, NH (US); Alexander Hartov, Enfield, NH (US); Lance G. Warhold, Norwich, VT (US)

(73) Assignee: Dartmouth-Hitchcock Clinic and The Trustees of Dartmouth College, Hanover, NH (US)

(*) Notice: Subject to any disclaimer, the term of this patent is extended or adjusted under 35 U.S.C. 154(b) by 370 days.

(21) Appl. No.: 16/018,218

(22) Filed: Jun. 26, 2018

Related U.S. Application Data

(60) Provisional application No. 62/525,158, filed on Jun. 26, 2017.

(51) Int. Cl.
| | |
|---|---|
| *A61B 17/88* | (2006.01) |
| *A61B 90/10* | (2016.01) |
| *A61B 90/11* | (2016.01) |
| *A61B 90/14* | (2016.01) |
| *A61B 34/10* | (2016.01) |
| *A61B 17/86* | (2006.01) |

(Continued)

(52) U.S. Cl.
CPC ........ *A61B 17/8897* (2013.01); *A61B 17/864* (2013.01); *A61B 34/10* (2016.02); *A61B 90/11* (2016.02); *A61B 90/14* (2016.02); *A61B 17/90* (2021.08); *A61B 2017/00526* (2013.01); *A61B 2017/564* (2013.01); *A61B 2034/107* (2016.02); *A61B 2090/3762* (2016.02)

(58) Field of Classification Search
CPC ..... A61B 17/8897; A61B 90/10; A61B 90/11; A61B 90/14
See application file for complete search history.

(56) References Cited

U.S. PATENT DOCUMENTS

| 3,017,887 A | * | 1/1962 | Heyer | ................... | A61B 90/11 604/175 |
| 3,103,926 A | * | 9/1963 | Cochran | ................ | A61B 17/72 606/319 |

(Continued)

FOREIGN PATENT DOCUMENTS

EP 2997926 A1 3/2016

*Primary Examiner* — Nicholas W Woodall
(74) *Attorney, Agent, or Firm* — Loginov & Associates, PLLC; William A. Loginov

(57) ABSTRACT

A system and method for installation of a k-wire through a scaphoid or other fractured bone can include a guide block for accurate trajectory of a k-wire. A support frame for a guide block can be casted and/or secured into place, and a CT scan is obtained, so the fractured bone and the location of the window can be known in the same three-dimensional space. An ideal k-wire trajectory can be plotted through the fractured bone, and a guide block with a lumen can be designed and printed using a three-dimensional printer. The guide block can be inserted into the frame so the lumen aligns with the ideal k-wire trajectory, and a k-wire can be inserted through the lumen into the fractured bone. The net effect would be ideal placement of the k-wire that would facilitate the ultimate insertion of a percutaneous screw to provide fixation of the fractured bone.

12 Claims, 18 Drawing Sheets

(51) Int. Cl.
  *A61B 90/00* (2016.01)
  *A61B 17/56* (2006.01)
  *A61B 17/00* (2006.01)
  *A61B 17/90* (2006.01)

(56) References Cited

U.S. PATENT DOCUMENTS

| | | | | |
|---|---|---|---|---|
| 4,821,716 A * | 4/1989 | Ghajar | ............... | A61B 17/1695 |
| | | | | 604/174 |
| 4,998,938 A * | 3/1991 | Ghajar | ................... | A61B 90/11 |
| | | | | 285/206 |
| 5,989,025 A * | 11/1999 | Conley | ................ | A61B 17/176 |
| | | | | 408/241 B |
| 6,328,748 B1 * | 12/2001 | Hennig | ............. | A61B 17/3403 |
| | | | | 606/130 |
| 6,902,569 B2 * | 6/2005 | Parmer | ................. | A61B 90/11 |
| | | | | 606/108 |
| 7,695,480 B2 * | 4/2010 | Solar | ..................... | A61B 90/11 |
| | | | | 606/130 |
| 9,033,990 B2 * | 5/2015 | Iannotti | ............. | A61B 17/1778 |
| | | | | 606/87 |
| 9,039,615 B2 * | 5/2015 | Flint | ........................ | A61B 8/12 |
| | | | | 600/437 |
| 9,351,780 B2 * | 5/2016 | Arthur | ............... | A61B 17/8855 |
| 9,486,193 B2 * | 11/2016 | Vidlund | ............. | A61B 17/0057 |
| 2012/0253353 A1 * | 10/2012 | McBride | ........... | A61B 17/1757 |
| | | | | 606/97 |
| 2014/0277209 A1 * | 9/2014 | Arthur | .............. | A61B 17/8816 |
| | | | | 606/86 R |

* cited by examiner

SYSTEM AND METHOD FOR SCAPHOID FIXATION

RELATED APPLICATION

This application claims the benefit of U.S. Provisional Application Ser. No. 62/525,158, entitled SYSTEM AND METHOD FOR SCAPHOID FIXATION, filed Jun. 26, 2017, the teachings of which application are expressly incorporated herein by reference.

FIELD OF THE INVENTION

This invention relates to percutaneous fixation of a fractured bone, and more particularly to a guide that allows for accurate placement of a k-wire, which provides the guide for placement of a cannulated screw that provides final fixation of the fracture

BACKGROUND OF THE INVENTION

Scaphoid fractures are among the most common fractures of the wrist. These fractures are often repaired by installing a percutaneous screw into the fractured bone. Correct placement of the percutaneous screw can be difficult, and sometimes can require multiple attempts at K-wire placement. Screw placement can be aided by a guide wire, known as a K-wire, which can be installed through the bone, and later removed after the screw has been placed. Doctors commonly use intraoperative fluoroscopy to help ensure correct placement of the K-wire and/or percutaneous screw. Current surgical techniques for treatment consist of placing a K-wire percutaneously and then inserting a cannulated screw over the K-wire. Placement of the K-wire can be difficult given the complex structure of the scaphoid bone, thereby causing increase surgical time, radiation exposure, and cost. It would be desirable to be able to install a K-wire and/or percutaneous screw in a single attempt thereby resulting in decreased surgical time and expense. It would further be desirable to correctly install the K-wire and/or percutaneous screw without exposing the patient and medical staff to repeated rounds of radiation from the fluoroscopic imaging that can occur through multiple attempts at K-wire placement. By decreasing the surgical time and increasing the efficiency of the procedure, an economic benefit would be seen by hospitals and payers of health care.

SUMMARY OF THE INVENTION

The present invention overcomes the disadvantages of the prior art by providing a system and method for designing a K-wire guide that can be customized to each patient. The present invention further provides a system and method for using the K-wire guide to correctly install a K-wire in a scaphoid bone in one attempt, without the need for reiterative placement, imaging, and placement adjustments. This system and method that ensures accurate placement can overcome disadvantages in the prior art by avoiding weakening the damaged bone with multiple holes, decreasing surgery time, reducing radiation exposure from fluoroscopic imaging, reducing the opportunity for surgeon error, and increasing efficacy of surgery, among other benefits.

In an embodiment, a system for installing a k-wire can include a guide block with a central lumen through the guide block, so that the central lumen is along a predetermined k-wire trajectory. The system can also include a support frame having at least one sidewall configured for holding the guide block. The support frame can be adapted to be held securely relative to a fractured bone of a patient, and the guide block can be designed to fit within the support frame, so that the central lumen of the guide block is aligned along the predetermined k-wire trajectory.

The system can include a cast, with the support frame adapted to be held in place relative to the patient's fractured bone by the cast. The support frame can include a brim. The at least one sidewall can define a block chamber that defines a first area near the brim that is smaller than a second area distant from the brim. The system can include a guide sleeve having a central lumen that is aligned along the predetermined k-wire trajectory. The guide block can include a frustum. The k-wire trajectory can define a predetermined path through the fractured bone.

In an embodiment, a method for installing a k-wire can include securing a support frame for a guide block relative to a fractured bone of a patient, obtaining a three-dimensional CT scan of the fractured bone and the support frame, with the scan containing the fractured bone and the support frame in the same three-dimensional space, plotting a trajectory for a k-wire through the fractured bone, with the trajectory in the same three-dimensional space, identifying the location of the support frame relative to the fractured bone and the trajectory in the three-dimensional space, designing a k-wire brace with a central lumen, so that the k-wire brace is designed to fit within the support frame, and so that the k-wire brace is aligned along the trajectory when the guide block is inserted within the support frame, preparing the k-wire brace, and securing the k-wire brace within the support frame The method can include installing a k-wire through the central lumen of the k-wire brace and through the fractured bone. The method can include installing a cannulated screw along the k-wire. Preparing a k-wire brace can include printing a guide block using a three-dimensional printer. Preparing a k-wire brace can include adjusting a stereotaxic instrument.

BRIEF DESCRIPTION OF THE DRAWINGS

The invention description below refers to the accompanying drawings, of which.

DETAILED DESCRIPTION

Figure 1A:
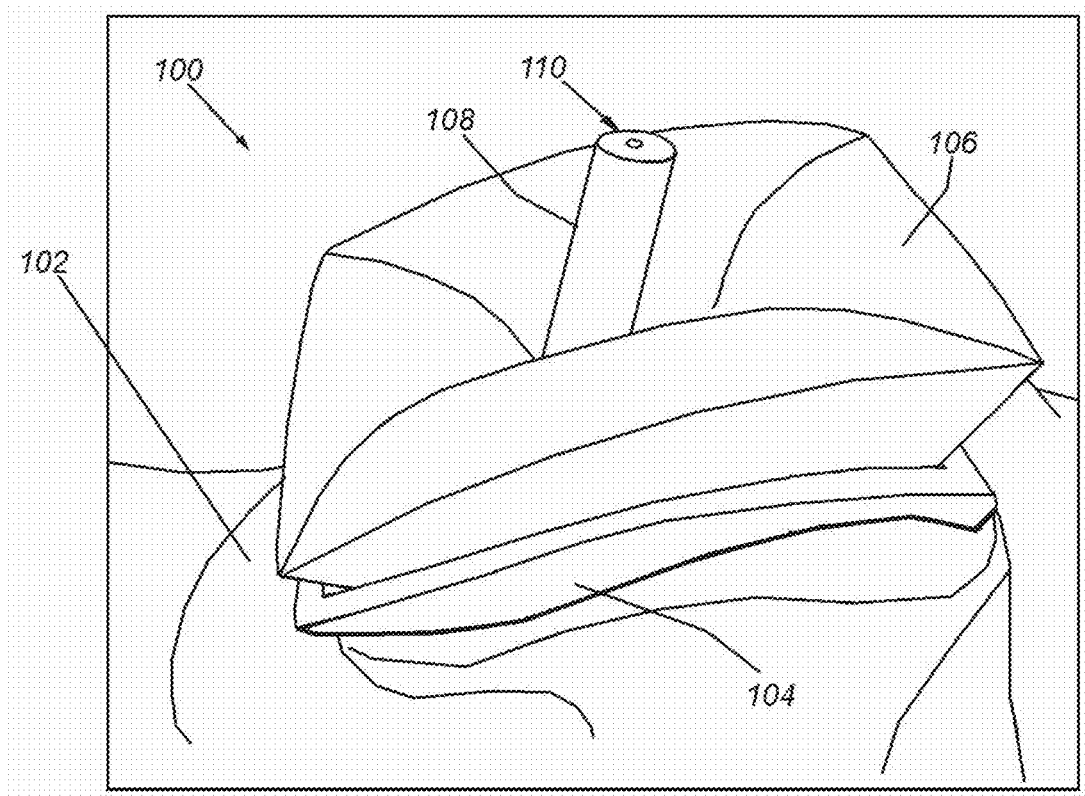
FIG. 1A is a perspective view of a k-wire guidance system with a guide block, according to an embodiment.

FIG. 1A is a perspective view of a k-wire guidance system with a guide block, according to an embodiment. In the illustrative embodiment, a k-wire guidance system 100 can include a cast 102, a guide frame 104, and a k-wire brace that can be a guide block 106. The cast 102 can be a common plaster cast, or other casting system as is known in the art for allowing bones to heal, or the cast can be another device to allow fixation of the guide frame to the arm. The cast can immobilize the wrist of a patient from the elbow to the fingers. The K-wire targeting device is secured in place relative to the fractured bone, and may consist of a cast or other device in order to secure it. A frame 104 can be placed against a patient's hand and/or wrist, and casting material can be wrapped around the patient's hand and lower arm, thereby securing the frame 104 in a fixed position against the patient's hand and/or wrist. A guide block 106 can be inserted into the frame 104, so that the guide block 106 is held in a fixed position relative to the patient's hand and/or wrist, so that the guide block 106 can also be in a fixed position relative to the bones in the patient's hand and wrist. The guide block 106 can have a guide sleeve 108. The guide sleeve 108 can have a k-wire lumen 110 that is sized to accommodate a k-wire, so that the k-wire can be inserted into the k-wire lumen 110 of the guide sleeve 108. The guide block 106 can maintain the k-wire in a fixed trajectory relative to the bones in the patient's hand and wrist. The k-wire can be inserted through the guide block 106, and can be further inserted into a bone of the patient, e.g. a scaphoid bone.

Figure 1B:
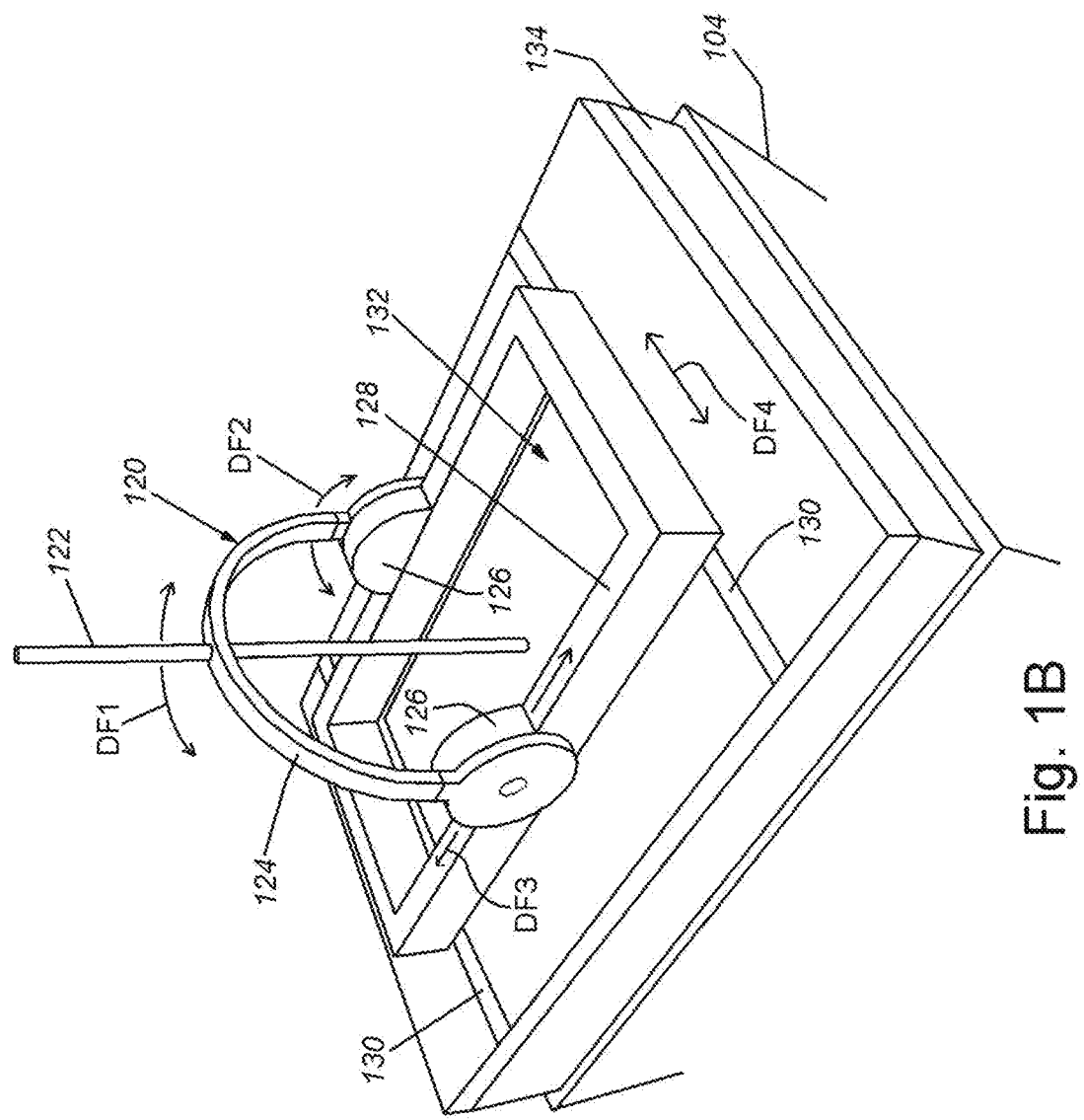
FIG. 1B is a perspective view of a k-wire guidance system with a stereotaxic instrument, according to an embodiment.

FIG. 1B is a perspective view of a stereotaxic instrument for a k-wire guidance system, according to an embodiment. In various embodiments a k-wire brace can be a stereotaxic instrument 120 that can be inserted into the guide frame 104 and held in a fixed position and orientation relative to a bone of the patient. The stereotaxic instrument 120 can be used to guide a k-wire along a predetermined trajectory through a scaphoid or other bone of the patient. The stereotaxic instrument 120 can have an adjustably positionable guide sleeve 122 that can be adjustably positioned through four or more degrees of freedom to be positioned along the desired trajectory.

In various embodiments, a guide sleeve 122 can move through a first degree of freedom along arrows DF1 by sliding along a first support 124. Guide sleeve 122 can slide within a channel in first support 124, or can have an extension that slidably engages with first support 124, or other means that will be obvious to one skilled in the art. Guide sleeve 122 can move through a second degree of freedom along arrows DF2 by pivoting the first support 124 relative to one or more second supports 126. Guide sleeve 122 can move through a third degree of freedom along arrows DF3 by sliding the one or more second supports 126 along one or more third supports 128. Guide sleeve 122 can move through a fourth degree of freedom DF4 by sliding the one or more second supports along one or more fourth supports 130. The stereotaxic instrument can have a central opening 132 that allows the guide sleeve and k-wire to pass through the central opening so that a surgeon can direct a k-wire through the stereotaxic instrument and into a scaphoid or other bone. The stereotaxic instrument can have a frustum portion 134 that can be sized and shaped to be held securely within the guide frame 104. In various embodiments, a stereotaxic instrument can have a wide variety of different types and arrangements of supports, pivots, sliders, hinges, or other components of a stereotaxic instrument that will be obvious to one skilled in the art.

A stereotaxic instrument 120 can have graduated markings along each degree of freedom, and can have clamps or other means for selectively allowing or prohibiting movement along each degree of freedom. A surgeon can use the graduated markings to guide the adjustment of the guide sleeve through multiple degrees of freedom into a predetermined position that can be along the desired k-wire trajectory. The stereotaxic instrument can be held in the guide frame in a known position relative to the bone of the patient, so that the guide sleeve 122 can be fixed securely along the desired trajectory relative to the scaphoid. The k-wire can then be inserted through the guide sleeve and into a bone of the patient.

Figure 2:
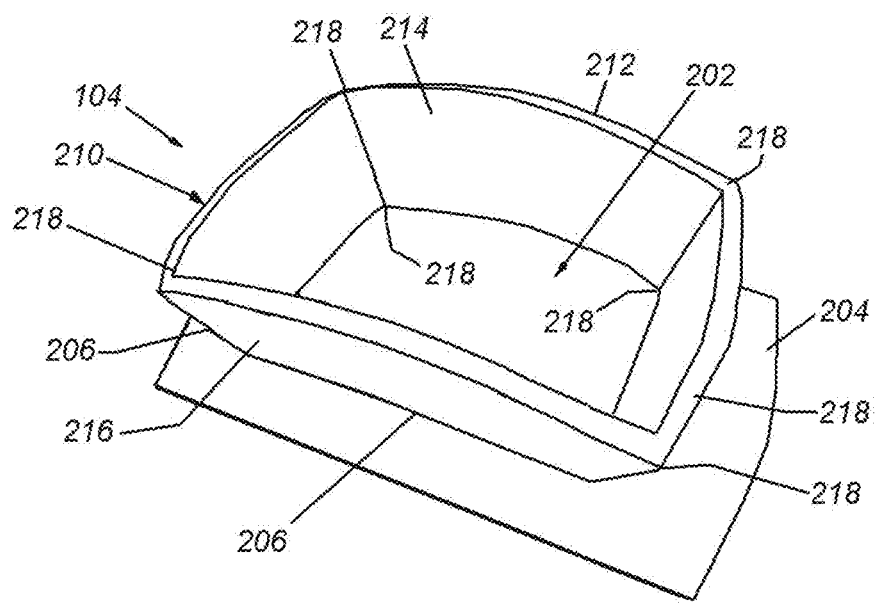
FIG. 2 is a perspective view of a support frame for a k-wire guide block, according to an embodiment.

FIG. 2 is a perspective view of a support frame for a k-wire guide block, according to an embodiment. In the illustrative embodiment, a support frame 104 can have a window 202, a brim 204, a waist 206, and a block holder 210. A support frame 104 for a k-wire guide block can be designed to be placed against the hand and/or wrist of a patient, and can be casted in place so that it can be held firmly in place relative to bones in the hand and/or wrist of the patient. The brim 204 can be shaped to rest securely against the hand and/or wrist of the patient. In an embodiment, the brim 204 can be convex. Casting material can overlay the brim 204, so that the casting material can hold the support frame 104 in place against the hand and/or wrist of the patient, and the casting material can prevent the support frame from being pulled out of the cast or moved relative to bones of the patient.

The support frame 104 can have a block holder 210 that extends above the brim 204. The block holder 210 can have at least one sidewall 212 that can hold a guide block 106 securely in place. A sidewall 212 can have an inner sidewall surface 214 and an outer sidewall surface 216. In an illustrative embodiment, the block holder 210 can define a quadrilateral window, and the block holder 210 can have four inner sidewall surfaces 214, but in alternate embodiments, the block holder 210 can define an oval-shaped window with a single sidewall, a triangular window with three sidewalls, or other various numbers or arrangements of sidewalls forming a window. In an embodiment, the window can be asymmetric, so that the guide block cannot be inserted incorrectly. In various embodiments, the frame can be free of sidewalls extending upwards from the brim. The frame can have a window that is free of surrounding sidewalls extending upwards, and the guide block can be inserted into the window of the frame without the need for upwardly-extending sidewalls to contact the guide block, and the guide block can be held in place through contact with the edges of the window. The frame can be a plate with a rectangular, triangular, or other appropriate window shape cut into the plate. The frame can have anchoring points on the frame that can be used to secure the guide block in the correct location, so that the guide block does not need to be held in place by sidewalls or the edges of the window.

In the illustrative embodiment of FIG. 2, the inner sidewall surfaces 214 can be angled upwards and outwards to accommodate a frustum-shaped portion of a guide block. The block holder 210 can define a block chamber that can be a space within the block holder adapted to hold a guide block. The block chamber can be frustum-shaped surrounding a smaller area near the brim and a larger area distant from the brim. The block holder 210 can have multiple reference points 218. The reference points 218 can be corners and/or edges of the block holder 210. In various embodiments, the reference points can be small stubs extending from the frame in known locations, embedded objects like pieces of steel in known locations that can easily be identifiable in CT, depressions in the frame in known locations, or other means for identifying reference points that will be obvious to those skilled in the art. In the illustrative embodiment, there can be eight reference points 218 that can be the top corners and bottom corners where each inner sidewall surface 214 meets other inner sidewall surfaces 214. The support frame can have a waist 206 where the outer sidewall surface 216 of the block holder 210 meets the top surface of the brim 206. Casting material, or other material used to hold the support frame in place, can abut the waist 206 and/or outer sidewall surfaces 216, so that the support frame 104 can be held securely by the cast in a fixed location relative to bones of the patient.

Figure 3:
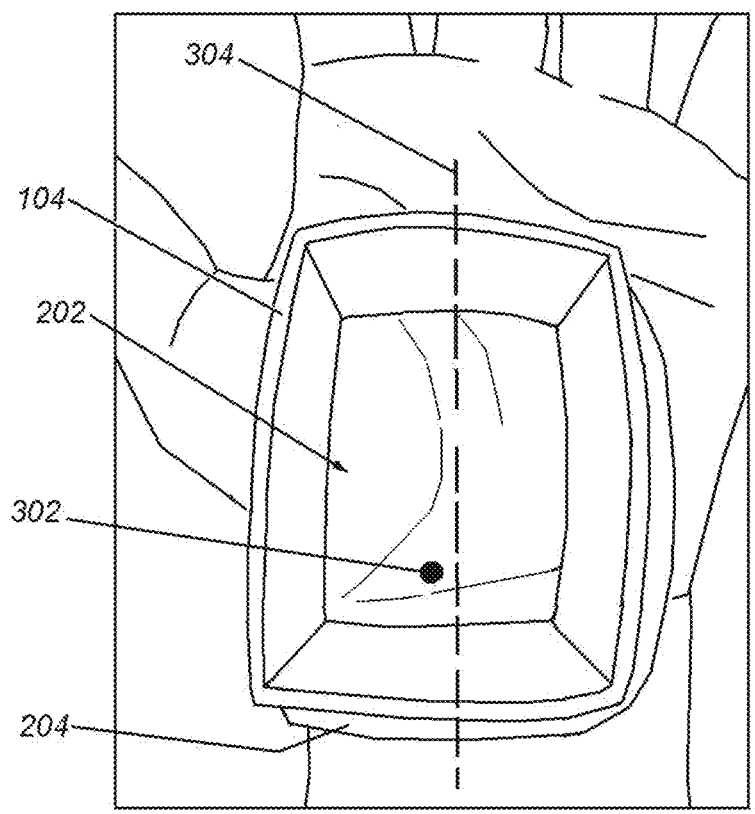
FIG. 3 is a perspective view of a support frame showing placement of the frame relative to a patient's wrist, according to an embodiment.

FIG. 3 is a perspective view of a support frame showing placement of the frame relative to a patient's wrist, according to an embodiment. A spot 302 can be marked on a patient's skin demonstrating the location of the scaphoid tubercle as an anatomic reference point. The patient's hand can be positioned with the fingers pointing up and the elbow pointing down, and the support frame can be positioned against the hand and/or wrist so that the brim 204 is adjacent to the patient's hand and/or wrist. The support frame can be positioned so that the spot 302 showing the scaphoid tubercle can be approximately near the central long axis 304 of the window 202, and the spot 302 can be approximately in the bottom third of the window 202. In various alternate embodiments, the support frame 104 can be designed to assist in repairing other fractured bones, and the window of the support frame can be positioned accordingly relative to a fractured bone to be repaired.

Figure 4:
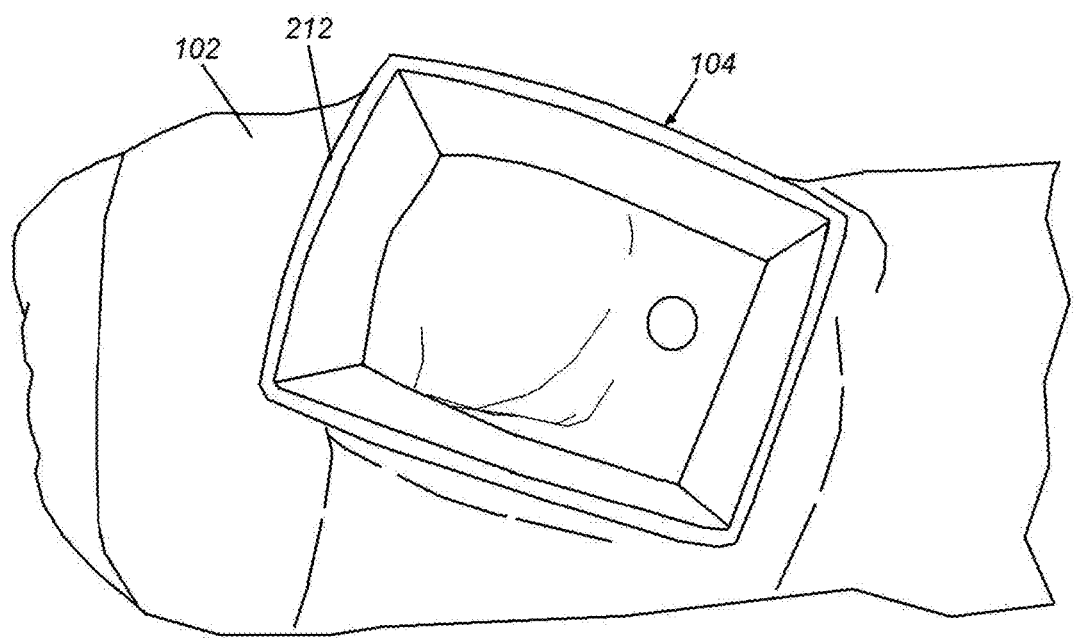
FIG. 4 is a perspective view of a cast holding a support frame in place on a patient's wrist, according to an embodiment.

FIG. 4 is a perspective view of a cast holding a support frame in place on a patient's wrist, according to an embodiment. Casting material can be used to form a cast 102 that can hold the support frame 104 securely in place relative to the fractured bone. In the illustrative embodiment, the cast can immobilize the hand, wrist, and arm from the fingers to the elbow, and can hold the frame securely in place against the hand and/or wrist. The casting material can overlay the brim and can abut the waist and/or sidewalls 212 to hold the support frame 104 in a fixed position relative to the fractured bone.

Figure 5:
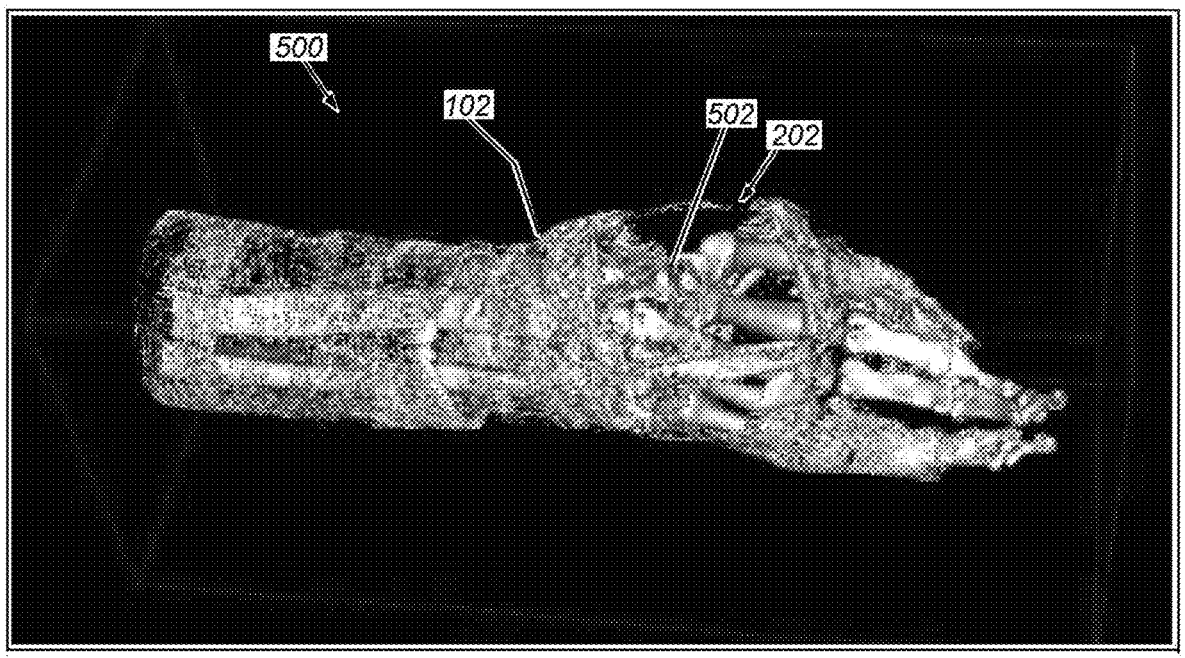
FIG. 5 shows a 3-dimensional reconstruction from a CT of a patient's wrist with a window casted in place on the wrist, according to an embodiment.

FIG. 5 shows a 3-dimensional reconstruction from a CT of a patient's wrist with a window casted in place on the wrist, according to an embodiment. After the window is embedded in the cast in an appropriate position and orientation, the patient's wrist can be scanned using a CT. The wrist can be scanned at a high resolution that can be, for example, approximately 0.6 mm or smaller depending on CT capabilities. A 3-dimensional reconstruction 500 of the patient's wrist can be created from the CT scan. As shown in FIG. 5, bones of the patient, including the scaphoid bone 502, can be seen in the 3-dimensional reconstruction. The cast 102 with the window 202 can also be seen in the 3-dimensional reconstruction. This 3-dimensional reconstruction 500 can provide data that can be used to create the guide block 106 for the k-wire.

A 3-dimensional reconstruction of the skeleton from a CT can be segmented to isolate a fracture. This can allow a surgeon or other medical provider to visualize the fracture. The segmentation of the skeleton can be done using a computer to highlight the fractured bone. The segmentation of the skeleton can be used to identify where a particular bone, such as the scaphoid, is located in a known three dimensional space.

The procedure can be based on thresholding of the bone while keeping other features out, such as the cast and window. Thresholding can isolate pixels or voxels that have values greater than a specified threshold. In x-ray CT, bone has higher attenuation and can usually be seen as very light (whiter) than the surroundings. By isolating bone pixels or voxels, it is possible to maintain a 3-dimensional view of the skeleton. Following thresholding it can be possible to remove from the visible set of pixels or voxels the pixels or voxels that are not part of the scaphoid to isolate the scaphoid and allow a medical provider to visualize the scaphoid alone in 3-dimensions. This can create a usable representation of the scaphoid in 3 dimensions, that can be either as a voxel volume or as a surface defined by nodes and facets, as will be understood by one skilled in the art.

Figure 6:
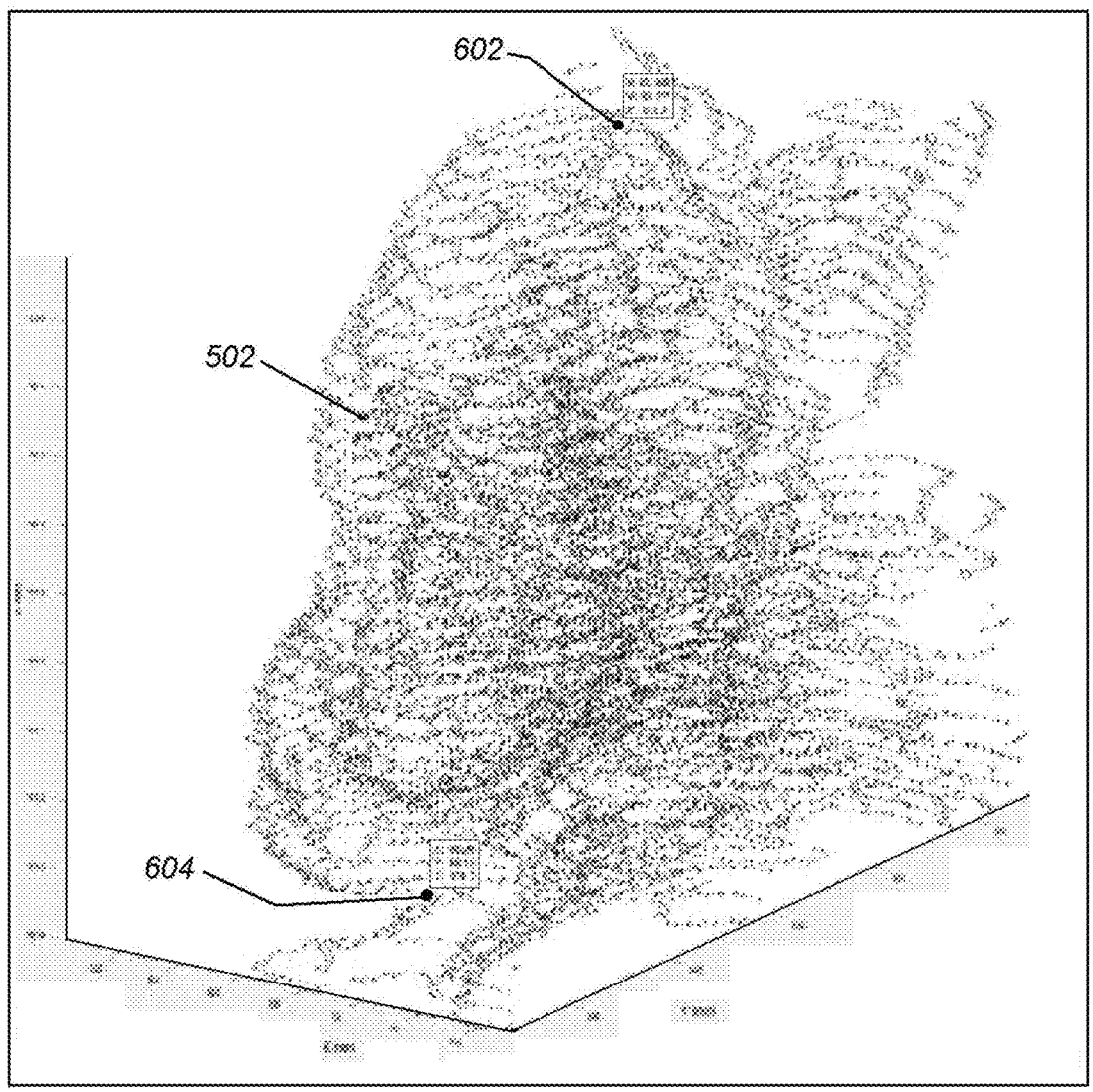
FIG. 6 shows a 3-dimensional reconstruction from a CT of a scaphoid bone with two points that define a trajectory for a k-wire through the scaphoid bone, according to an embodiment.

FIG. 6 shows a 3-dimensional reconstruction from a CT of a fractured scaphoid bone, with two points that define a trajectory for a k-wire through the scaphoid bone, according to an embodiment. As shown in the exemplary embodiment of FIG. 6, the skeleton has been segmented to isolate the scaphoid bone 502, which can be visualized in 3 dimensions. An entry point 602 and an exit point 604 can be identified on the bone. The entry point 602 and exit point 604 can define a trajectory for the k-wire. It should be clear that the insertion of the k-wire could be performed from either side of the wrist, and the k-wire could enter or exit through either of the entry point 602 and exit point 604. For the sake of clarity, the method defined herein describes insertion of the k-wire through the palm and entering the scaphoid through entry point 602, however an opposite trajectory entering through exit point 604 and exiting through entry point 602 is specifically contemplated.

Figure 7:
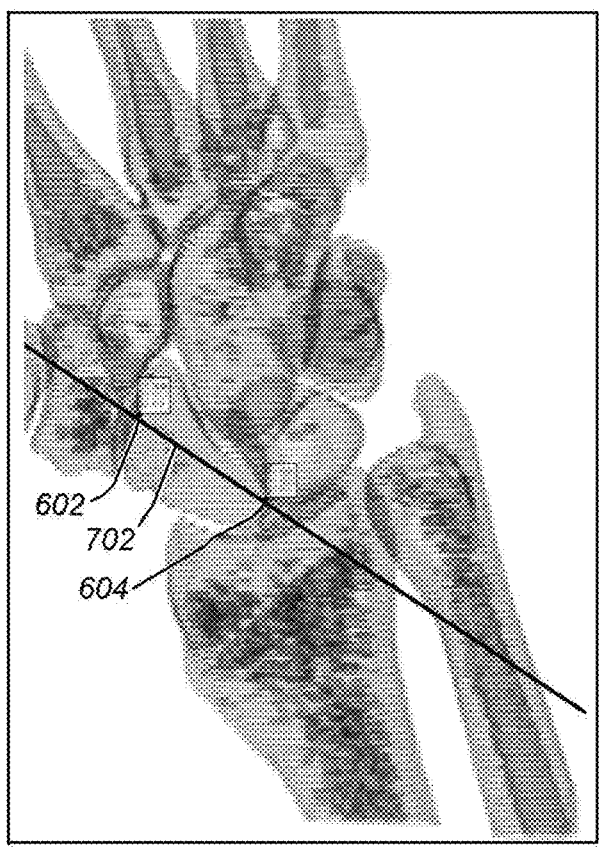
FIG. 7 shows a reconstruction from a CT of a skeleton showing a trajectory for a k-wire through a scaphoid bone, according to an embodiment.

FIG. 7 shows a reconstruction from a CT of a skeleton showing a trajectory for a k-wire through a scaphoid bone, according to an embodiment. The entry point 602 and exit point 604 define a trajectory line 702. Trajectory line 702 shows an intended trajectory for a k-wire through a scaphoid bone. The trajectory line 702 can be placed in the central ⅓ axis of the scaphoid without breaching the cortical bone, as would be obvious to a surgeon or radiologist skilled in k-wire placement.

Figure 8:
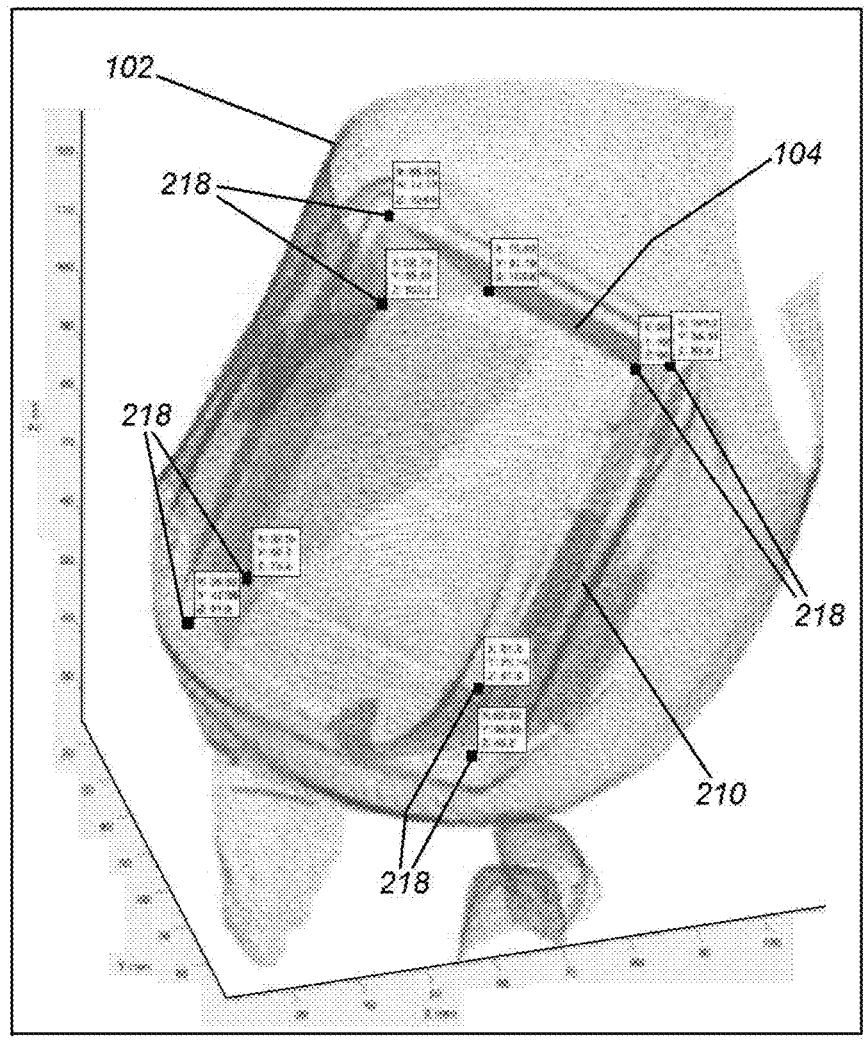
FIG. 8 shows a reconstruction from a CT of a frame fixed in a cast and showing reference points on the frame to be used in creating a 3-dimensional model of a guide block, according to an embodiment.

FIG. 8 shows a reconstruction from a CT of a frame fixed in a cast and showing reference points on the frame to be used in creating a 3-dimensional model of a guide block, according to an embodiment. The 3-dimensional CT of the cast 102, the support frame 104, and the partial skeleton, as shown in FIG. 5 can be segmented to isolate the cast 102 and the support frame 104. Because the material of the support frame can be less dense than bone, a lower thresholding value can be used to isolate the support frame. The support frame 104 can be isolated to obtain a 3-dimensional representation of the frame 104, including the block holder 210. Isolating the frame 104 can allow a guide block 106 to be designed to fit within the frame 104. The reference points 218 of the support frame can be identified in the 3-dimensional reconstruction of the CT. Identifying the location of the eight reference points 218 in the 3-dimensional space allows the locations of the four section planes, or inner sidewall surfaces 214, to be known. In alternate embodiments, a window with a different shape is possible, and identification of reference points can allow the locations of the at least one inner sidewall surface to be known.

The four inner sidewall surfaces 214 in the present embodiment can represent a section of a frustum. After the locations of the inner sidewall surfaces 214 have been identified in the 3-dimensional space through identification of the reference points 218, a section of a frustum can be identified in the 3-dimensional space through the identification of the inner sidewall surfaces 214. The frustum defined by the inner sidewall surfaces 214 can form the basis for designing the guide block 106.

Figure 9:
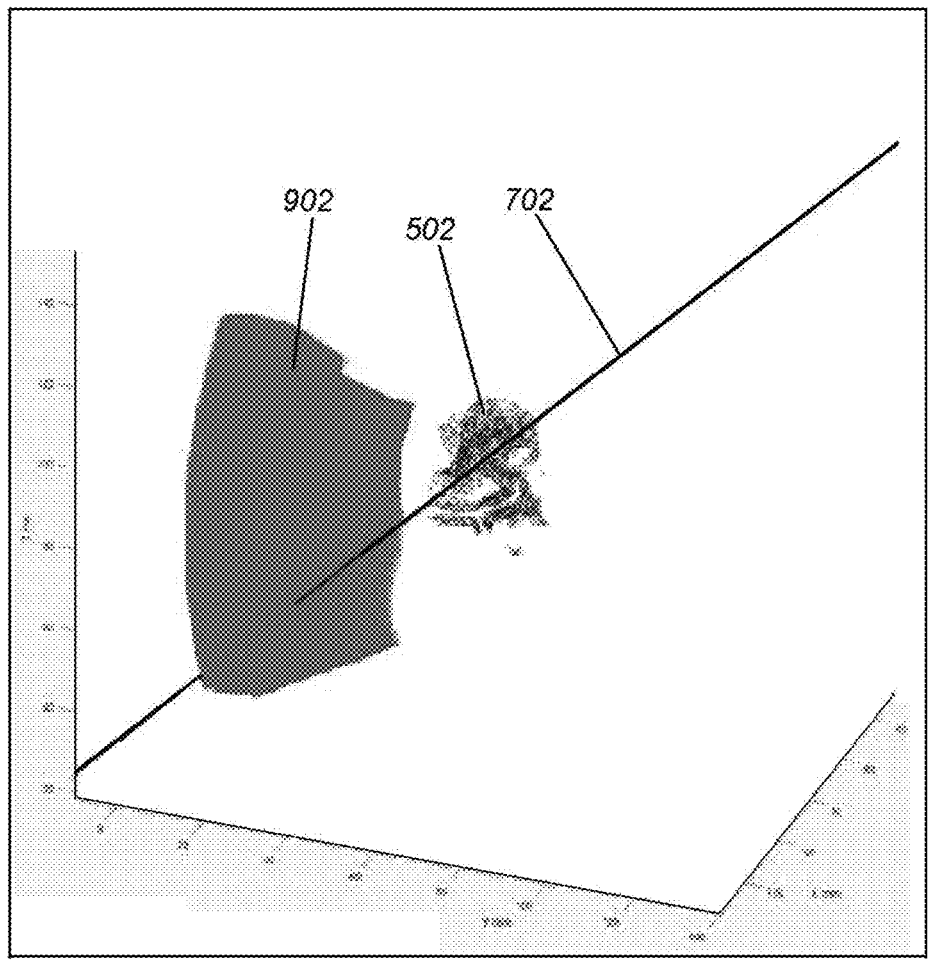
FIG. 9 shows a side view of a 3-dimensional model of a guide block and a scaphoid bone with a k-wire trajectory passing through the scaphoid bone and the guide block, according to an embodiment.

FIG. 9 shows a side view of a 3-dimensional model of a guide block and a scaphoid bone with a k-wire trajectory passing through the scaphoid bone and the guide block, according to an embodiment. Because the location of the scaphoid bone 502, the location of the intended k-wire trajectory 702, and the location of the frustum defined by the inner sidewall surfaces are all known in the same 3-dimensional space, a 3-dimensional model of a guide block 902 can be designed to fit securely in the window with the intended k-wire trajectory 702 passing through the 3-dimensional model of the guide block 902. The thickness of the model of the guide block 902 can be designed so that it does not extend below the sidewall inner surfaces 214 and/or does not occupy the same space as the patient's hand and/or wrist. The thickness of the model of the guide block 902 can extend as far out from the patient as desired to ensure adequate guidance of the k-wire.

Figure 10:
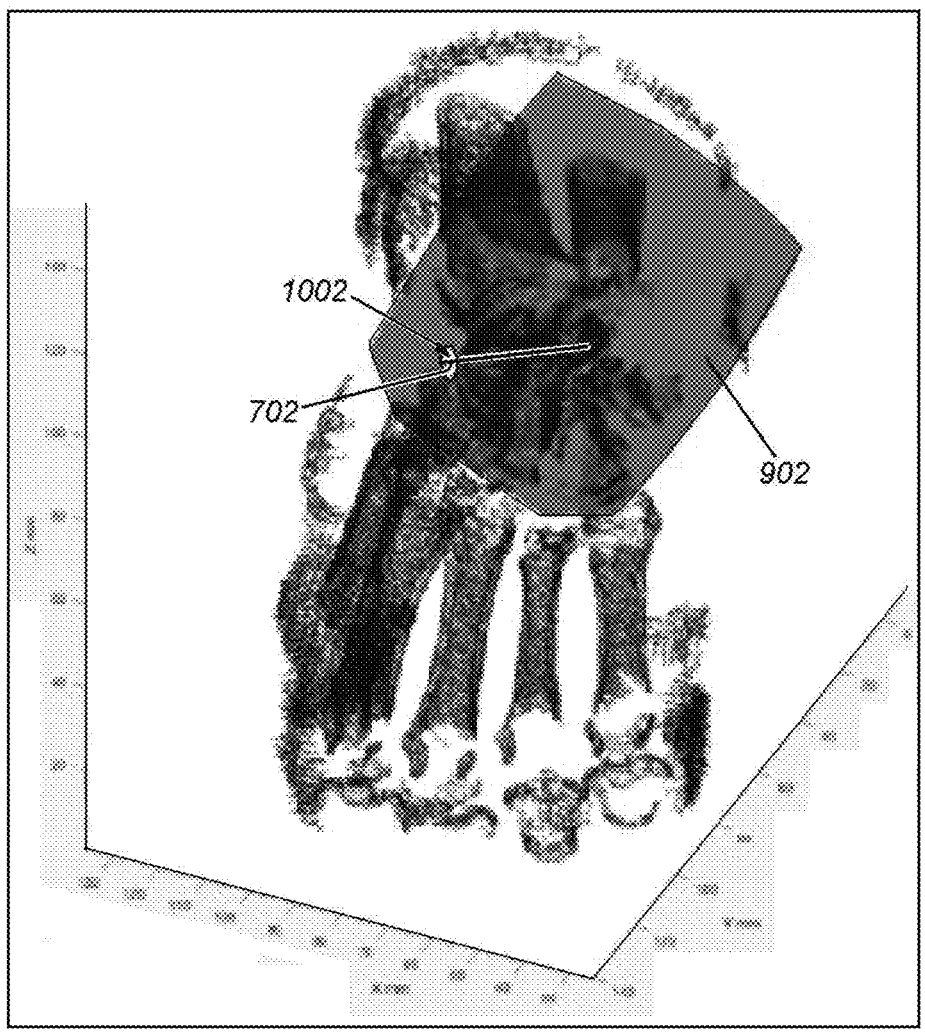
FIG. 10 shows a top view of a 3-dimensional model of a guide block and a skeleton with a k-wire trajectory passing through the scaphoid bone and the guide block, according to an embodiment.

FIG. 10 shows a top view of a 3-dimensional model of a guide block and a skeleton with a k-wire trajectory passing through the scaphoid bone and the guide block, according to an embodiment. The three dimensional representation of the guide block 902 is shown with a guide sleeve cavity 1002. The guide sleeve cavity 1002 can be designed so that a guide sleeve with a k-wire lumen can be inserted into the guide sleeve cavity 1002 in the guide block. In embodiments without a guide sleeve, a k-wire lumen can pass entirely through the guide block. The 3-dimensional representation of a guide block 902 can be designed with a guide sleeve cavity 1002 so that the intended k-wire trajectory 702 passes through the guide sleeve cavity 1002. This three dimensional model of a guide block 902 can then be used to create a physical guide block 106. The physical guide block, which is based on the 3-dimensional model 902, can be designed to be sized and shaped to fit securely and precisely within the window of the frame, and the guide sleeve cavity 1002 can be sized and shaped for the guide sleeve to fit securely and precisely within the guide sleeve cavity 1002. The guide block can also be designed, based on the model 902, with the intended k-wire trajectory passing through a k-wire lumen in the guide block, so that k-wire lumen can be used to guide the k-wire along the desired trajectory through the scaphoid bone. In various embodiments, the guide block can have a guide sleeve cavity 1002 extending all the way through the guide block, so that a guide sleeve can be inserted all the way through the guide block, and the k-wire lumen can pass through the guide sleeve, or the guide block can be free of a guide sleeve and can have the k-wire lumen extending all the way through the guide block, so that the k-wire trajectory can pass through the k-wire lumen. In an embodiment, the guide sleeve cavity can extend from the top of the guide block and partially through the guide block with the bottom of the guide sleeve cavity at a known depth in the guide block, and a k-wire lumen can extend through the guide sleeve, and from the bottom of the guide sleeve cavity to the bottom of the guide block, so that the k-wire trajectory can pass through the guide sleeve and through the guide block.

Figure 11:
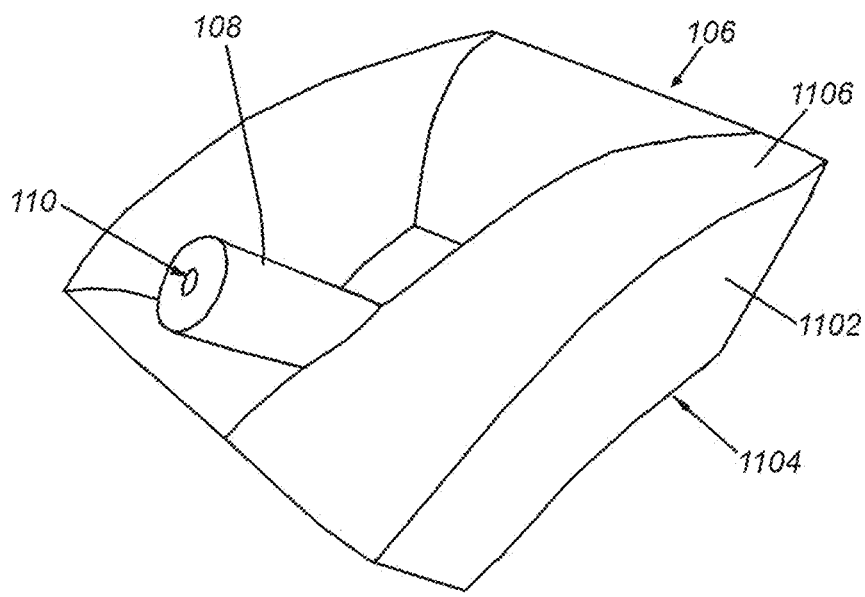
FIG. 11 shows a perspective view of a guide block with a guide sleeve;
according to an embodiment.

FIG. 11 shows a perspective view of a guide block with a guide sleeve; according to an embodiment. A guide block 106 can be printed by a 3-dimensional printer based on the 3-dimensional model 902. The guide block 106 can have outer block walls 1102 that can define a frustum portion 1104 of the guide block 106. The frustum portion 1104 can be wider at the top and narrower near the patient. The frustum portion shown in FIG. 11 is depicted with planar sides, however, it should be clear that the sides can be curved, or stepped, or have other shapes that are wider at the top and narrower at the bottom, so that they can be held securely by the support frame in a known orientation. The top and/or bottom of the frustum portion can be planar, or can be curved or other non-planar shapes. The frustum portion 1104 is sized and shaped to be held securely within the window of the guide frame. The guide block can have a top surface 1106, and the top surface 1106 can include a guide sleeve 108. The guide sleeve 108 can have a k-wire lumen 110 sized and shaped to accommodate a k-wire. In the embodiment shown in FIG. 11, the guide block 106 can be printed with a guide sleeve cavity extending from the top surface 1106 through at least a portion of the guide block 106. The guide sleeve cavity can be designed for a guide sleeve 108 to be inserted into the guide sleeve cavity. The guide sleeve cavity can be a cylindrical hole, square hole, or other hole designed to accommodate a guide sleeve 108 within the guide block 106, so that the guide sleeve 108 can be inserted into the guide sleeve cavity and the guide sleeve 108 can extend through at least a portion of the guide block 106. The k-wire lumen 110 through the guide sleeve, and the k-wire lumen 110 through the guide block can be aligned so that the intended k-wire trajectory passes through both the guide sleeve 108 and the guide block. Alternately, the guide sleeve 108 can extend all the way through the guide block, and the k-wire lumen 110 can extend through the guide sleeve 108. The guide block 106 can be inserted securely into the window of the guide frame, and when the guide block 106 is secured in the guide frame, the intended trajectory of the k-wire can pass through the k-wire lumen 110, and the entry point 602 and exit point 604 of scaphoid bone 502. In various embodiments, the guide block can be printed with the guide sleeve 108 as a unitary part of the guide block 106, and the k-wire lumen 110 will be aligned along the intended k-wire trajectory. In another embodiment, the guide block can be free of a guide sleeve, and the k-wire lumen will extend through the guide block 106 from the bottom of the guide block to the top surface 1106 of the guide block 106. In another embodiment, the guide sleeve cavity can extend through the guide block from the top surface 1106 to the bottom of the guide block, and the k-wire lumen can pass through the guide sleeve. In another embodiment, the guide sleeve cavity can extend partially through the guide block, and the k-wire lumen can extend through the guide sleeve and through the guide block.

Because the locations and geometries of the guide block 106, which can include a guide sleeve 108, plus the entry point 602 and exit point 604 of the scaphoid bone 502 are all known in the same 3-dimensional space, the correct insertion length of k-wire can also be known. The maximum insertion length of k-wire can be known from the 3-dimensional recreation so that the k-wire does not extend beyond the exit point 604 to a distance that would cause injury to nearby bones, such as the radius. This maximum insertion length of k-wire can be the distance from the exit point 604 to the top of the guide block 106, which can be the top of the guide sleeve 108. The maximum insertion length can then be measured and marked on the k-wire prior to insertion of the k-wire into the lumen(s) and into the scaphoid. When the k-wire has been inserted to the maximum depth, the mark will be at the top of the guide block 106, which can be the top of the guide sleeve 108.

Figure 12A:
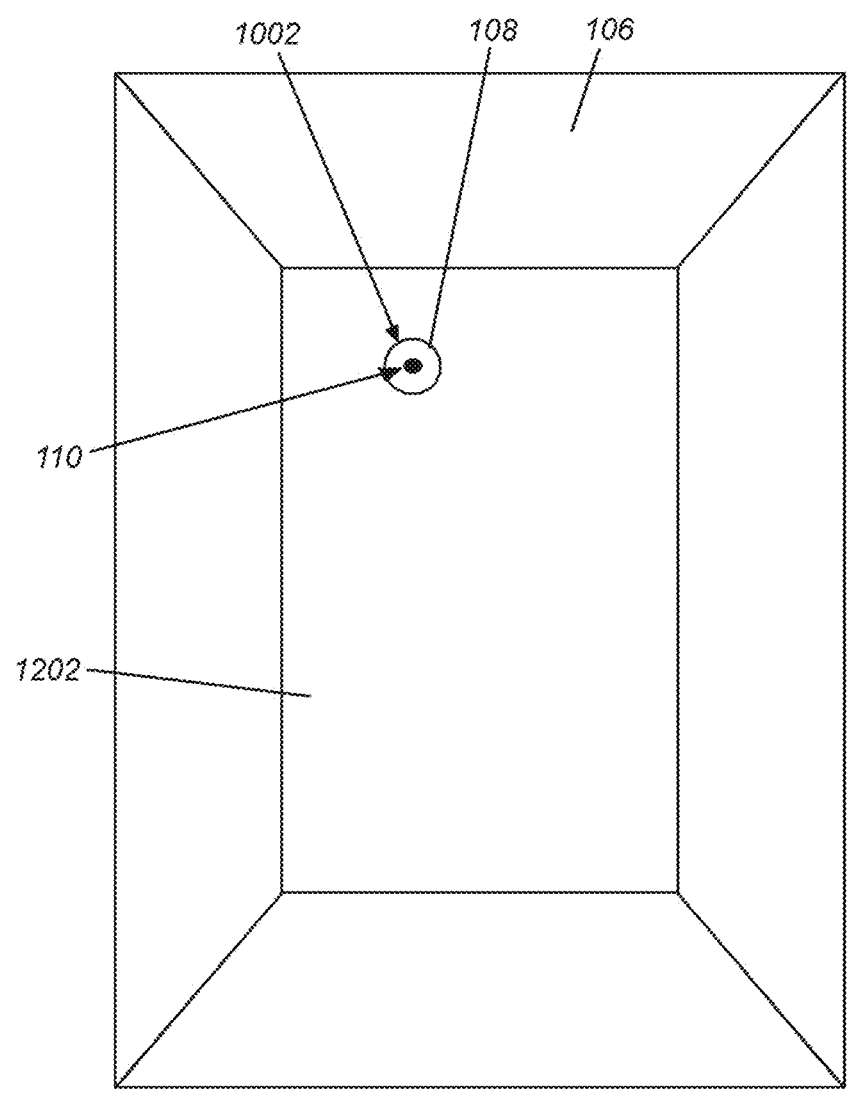
FIG. 12A shows a bottom view of a guide block with a guide sleeve, according to an embodiment.

FIG. 12A shows a bottom view of a guide block with a guide sleeve, according to an embodiment. The guide block 106 can have a bottom surface 1202. The guide sleeve cavity 1002 can be seen in FIG. 12 extending through the guide block to the bottom surface 1202 of the guide block 106. A guide sleeve 108 with a k-wire lumen 110 can be inserted into the guide sleeve cavity 1002. The bottom surface 1202 is designed to be inserted into the window of the support frame so that the bottom surface 1202 is facing the skin of the patient. The k-wire can pass through the guide sleeve 108 that is within the guide sleeve cavity 1002, through the skin of the patient, and into the entry point 602.

Figure 12B:
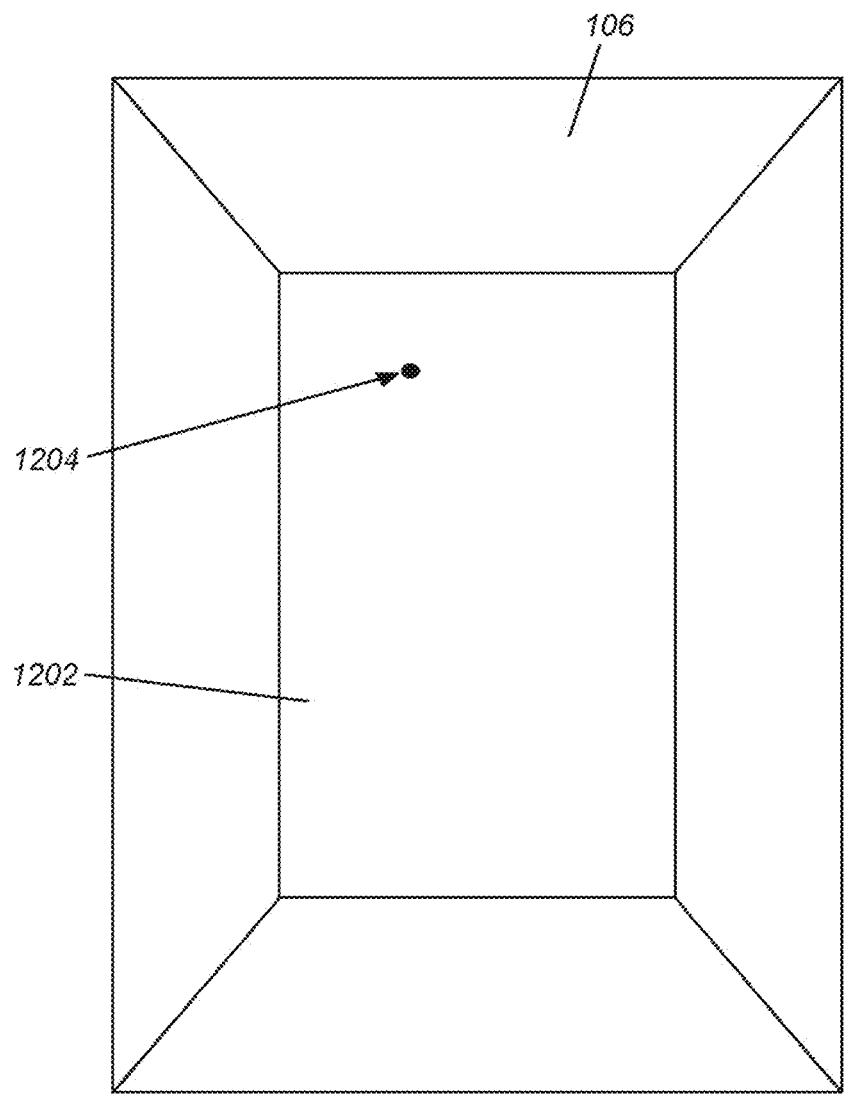
FIG. 12B shows a bottom view of a guide block with a k-wire lumen, according to an embodiment.

FIG. 12B shows a bottom view of a guide block with a k-wire lumen, according to an embodiment. The guide block 106 can have a bottom surface 1202, and can have a k-wire lumen 110 extending through the bottom surface 1202. The guide block can be free of a guide sleeve, so that the k-wire lumen 110 extends entirely through the guide block 106, or the guide block 106 can have a guide sleeve cavity that extends partially through the guide block, and can have a k-wire lumen 110 that extends from the bottom of the guide sleeve cavity to the bottom of the guide block.

In various embodiments of a k-wire guidance system having a k-wire brace that is a stereotaxic instrument, a 3-dimensional model of a k-wire brace can include the guide sleeve positioned along the desired k-wire trajectory. Because the position of bone, the desired trajectory, the guide frame, and k-wire brace can all be known in a fixed space relative to each other, the correct positioning of the guide sleeve along the k-wire trajectory can be determined in the 3-dimensional model. The correct adjustment of each of the degrees of freedom can then be determined based on the modeled position of the guide sleeve. A surgeon can use the graduated markings on the stereotaxic instrument to adjust the physical guide sleeve into alignment with the guide sleeve of the 3-dimensional model. In various embodiments, the 3-dimensional modeling can include a numeric output indicating the correct adjustment for each degree of freedom. By way of non-limiting example, the output could indicate that the first degree of freedom should be fixed at 20 mm left of center, the second degree of freedom should be fixed at 37 degrees back from center, etc. A surgeon can then use the numeric output from the 3-dimensional modeling of the scaphoid and desired trajectory to adjust the stereotaxic instrument so that the guide sleeve will be aligned with the desired trajectory.

Figure 13:
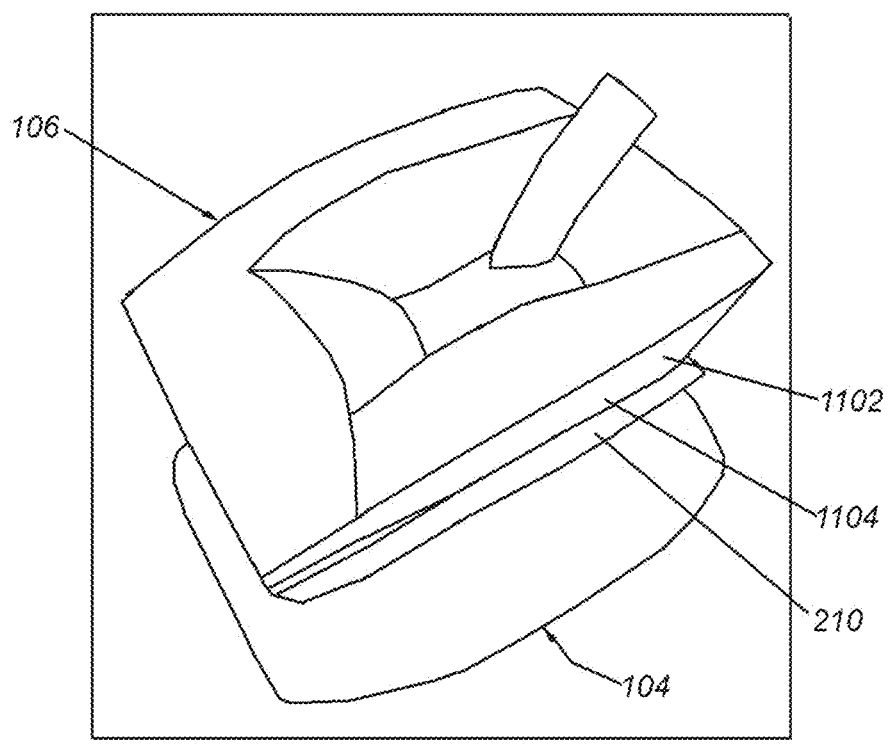
FIG. 13 shows a perspective view of a guide block held within a support frame, according to an embodiment.

FIG. 13 shows a perspective view of a guide block held within a support frame, according to an embodiment. Although the k-wire brace is shown and described as a guide block in FIGS. 13-17, it should be clear that in various embodiments the k-wire brace could be a stereotaxic instrument. The outer block walls 1102 can be in contact with the inner sidewall surfaces of the support frame 104, so that at least a portion of the frustum portion 1104 of the guide block 106 is held securely within the block holder 210 of the support frame 104.

Figure 14:
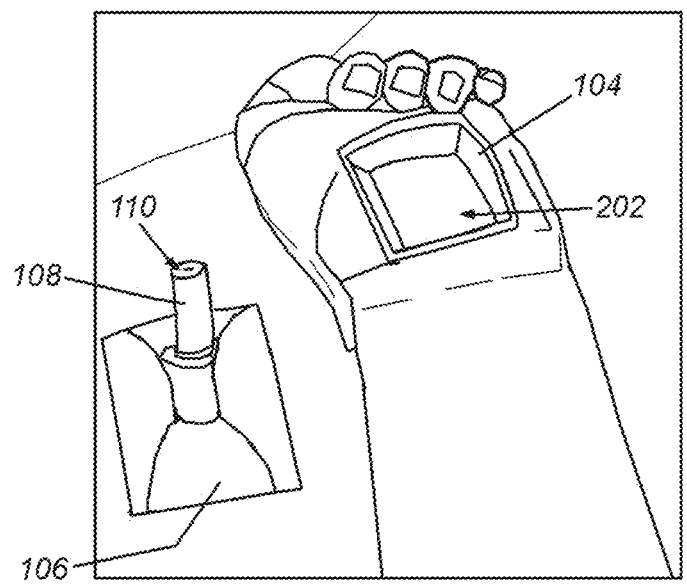
FIG. 14 shows a perspective view of a patient's wrist with a window casted in place, and a support block with a sleeve, according to an embodiment.

FIG. 14 shows a perspective view of a patient's wrist with a window casted in place, and a support block with a sleeve, according to an embodiment. A surgeon or other medical provider can place the support frame 104 against the hand and wrist of the patient, and the medical provider can cast the support frame 104 securely in place relative to the hand and wrist. A 3-dimensional CT scan can then be taken, and the scaphoid bone can be isolated in the known 3-dimensional space so that the physician or other medical provider can determine an entry point and exit point for a k-wire. An intended trajectory for the k-wire can be plotted between the entry point and the exit point in the known 3-dimensional space. The reference points on the support frame can be located so that the location of the window of the support frame can be known in the same 3-dimensional space. A guide block model can be designed that will fit securely within the window, and the guide block model can have a k-wire lumen and/or guide sleeve cavity that accommodates the intended k-wire trajectory. A physical guide block 106 can be manufactured that has a k-wire lumen and/or guide sleeve cavity for a guide sleeve that accommodates the k-wire trajectory when the guide block 106 is fit securely in the window. The guide block 106 as shown in FIG. 14 can be manufactured with a guide sleeve cavity 1102, a guide sleeve 108, and a k-wire lumen 110. The guide block 106 is ready to be inserted into the window 202.

Figure 15:
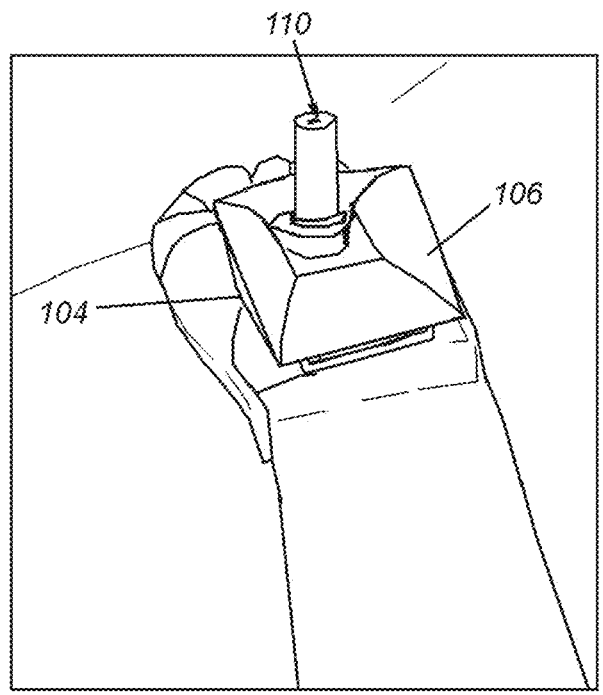
FIG. 15 shows a perspective view of a patient's wrist with a window casted in place, and a support block with a sleeve held in place within the window, according to an embodiment.

FIG. 15 shows a perspective view of a patient's wrist with a window embedded in place in the cast, and a support block with a sleeve held in place within the window, according to an embodiment. As shown in FIG. 15, the guide block 106 has been inserted into place within the window of the support frame 104. The k-wire lumen 110, and the entry point and exit point on the scaphoid bone of the patient are now aligned along the intended k-wire trajectory.

Figure 16:
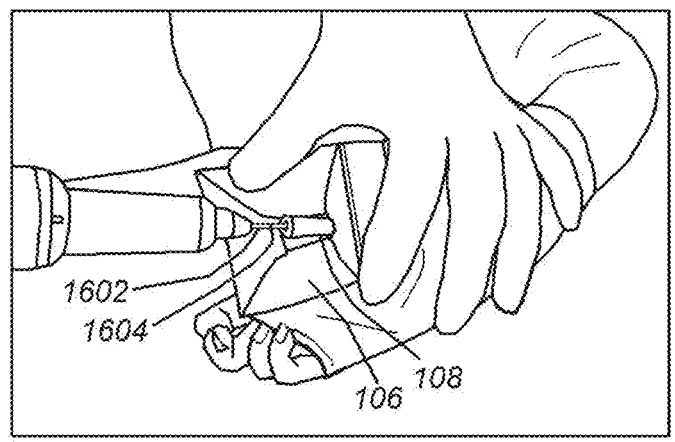
FIG. 16 shows a perspective view of a k-wire being inserted through a guide sleeve and into the scaphoid bone, according to an embodiment.

FIG. 16 shows a perspective view of a k-wire being inserted through a guide sleeve and into the scaphoid bone, according to an embodiment. A physician or other medical provider can insert a k-wire 1602 through the k-wire lumen, and the k-wire lumen will maintain the k-wire in the intended k-wire trajectory through the entry point and the exit point of the scaphoid. Because the locations and geometries of the guide block 106, the top of the guide sleeve 108, and the exit point of the scaphoid bone are all known in the same 3-dimensional space, the correct insertion length of k-wire can be known to the surgeon or other medical provider before the k-wire is inserted. Before the k-wire is inserted, the physician or other medical provider can determine from the 3-dimensional recreation how many millimeters of k-wire should be inserted through the top of the guide sleeve to reach the ideal depth through the scaphoid bone without extending through the scaphoid bone to a distance that may cause damage to nearby bones. The ideal depth line 1604 can be measured and marked on the k-wire 1602, so that the surgeon or other medical provider will know that the ideal depth has been reached when the k-wire has been inserted until the depth line 1604 reaches the top of the guide sleeve. In embodiments that are free of a guide sleeve, the measurement can be taken from the place where the guide block lumen meets the top of the guide block.

Figure 17:
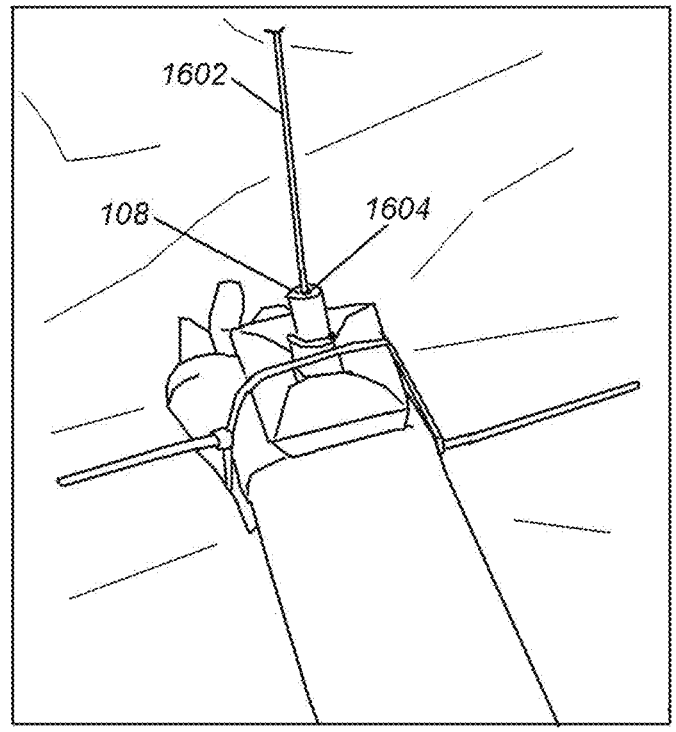
FIG. 17 shows a perspective view of a patent's casted wrist with an inserted k-wire extending through the guide block and guide sleeve, according to an embodiment.

FIG. 17 shows a perspective view of a patent's casted wrist with an inserted k-wire extending through the guide block and guide sleeve, according to an embodiment. The k-wire 1602 has been inserted along the intended k-wire trajectory through the sleeve lumen, the guide block lumen, and the scaphoid, until the depth line 1604 has reached the top of the guide sleeve 108. The k-wire has been properly installed along the intended trajectory, and only one hole has been drilled through the scaphoid.

Figure 18:
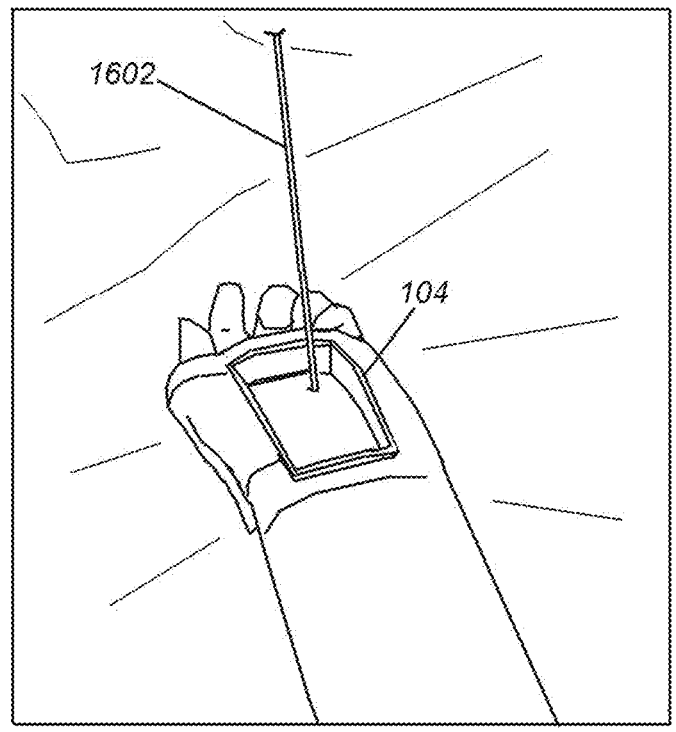
FIG. 18 shows a perspective view of a patient's casted wrist with the guide block removed and with an inserted k-wire extending from the palm, according to an embodiment.

FIG. 18 shows a perspective view of a patient's casted wrist with the guide block removed and with the inserted k-wire extending from the palm, according to an embodiment. After the k-wire 1602 has been properly inserted along the intended trajectory, the guide block can be removed from the support frame 104, and the guide block can be slid along the k-wire 1602 until the guide block is free from the k-wire.

Figure 19:
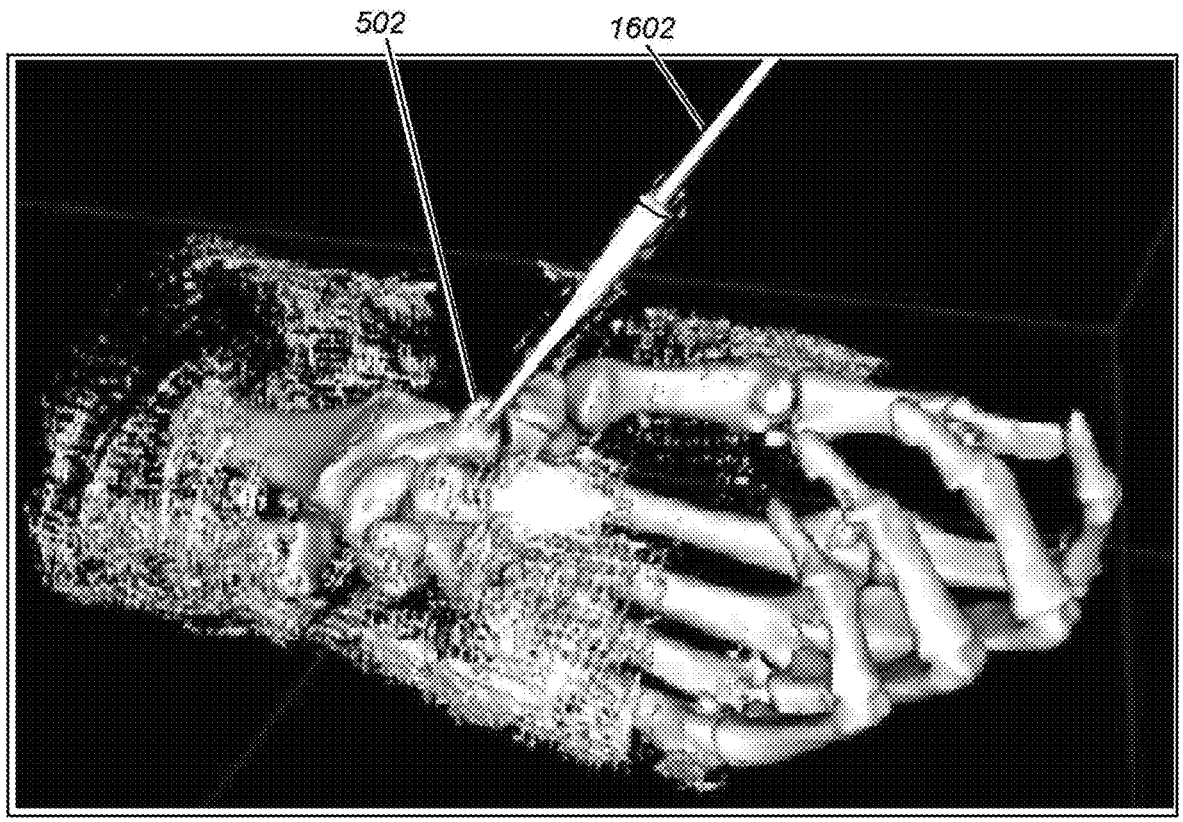
FIG. 19 shows a perspective view from a CT showing a k-wire that has been properly installed through a scaphoid bone.
Figure 20:
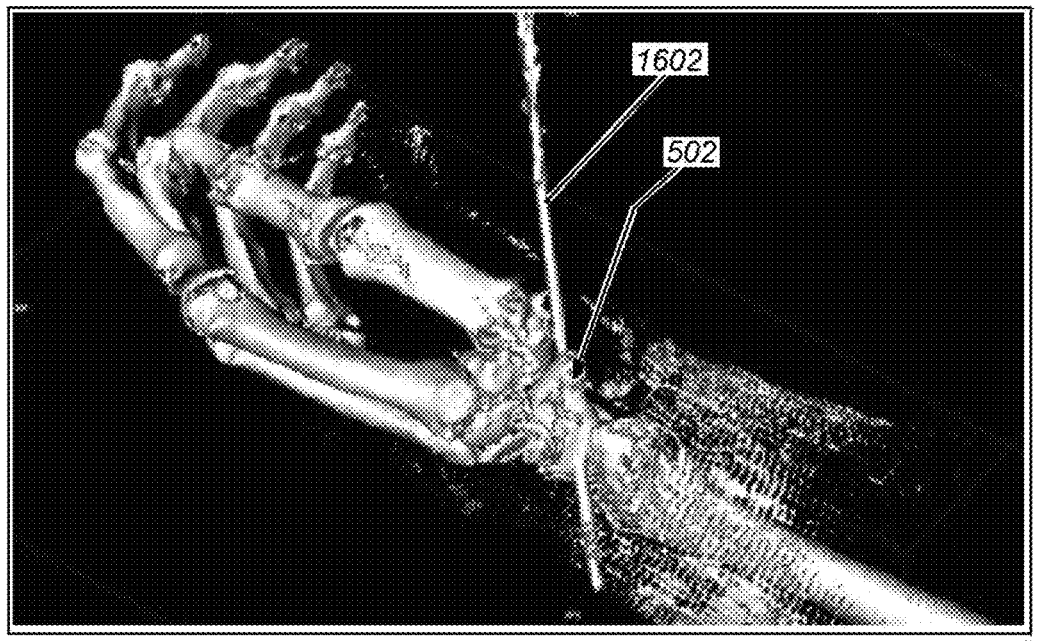
FIG. 20 shows a different perspective view from a CT showing a k-wire that has been properly installed through a scaphoid bone.

FIGS. 19 and 20 show perspective views from a CT showing a k-wire that has been properly installed through a scaphoid bone. After the k-wire 1602 has been installed, a medical provider can take at least one new x-ray, CT, or other images showing the trajectory of the k-wire 1602. These images can allow the surgeon or other medical provider to verify that the k-wire has been properly guided along the desired trajectory through the bone 502. As shown in FIG. 20, the k-wire 1602 can extend safely beyond the exit point of the scaphoid bone 502 if the k-wire does not impact other nearby bones.

Figure 21:
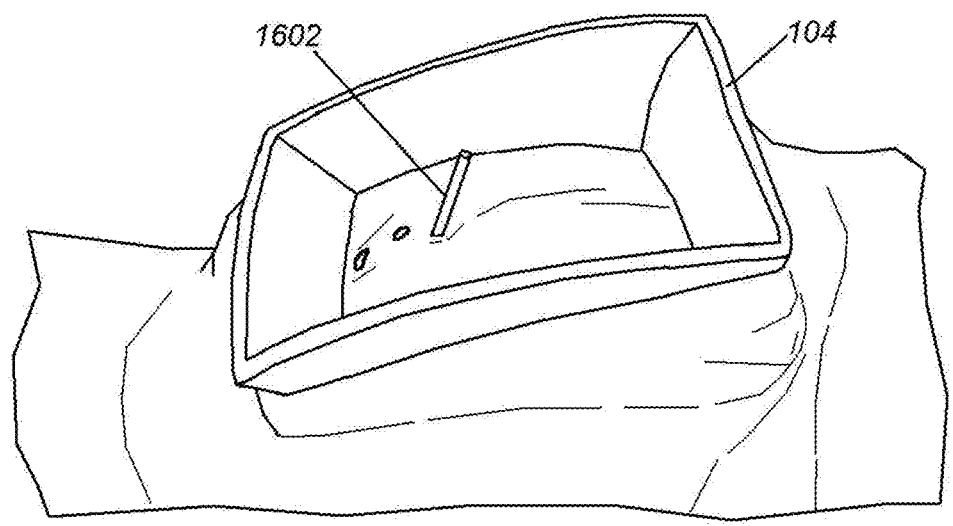
FIG. 21 shows a perspective view of a patient's casted wrist with an inserted k-wire that has been cut for use as a guide for a percutaneous screw, according to an embodiment.

FIG. 21 shows a perspective view of a patient's casted wrist with an inserted k-wire that has been cut for use as a guide for a percutaneous screw, according to an embodiment. The k-wire 1602 can be cut to a length that is convenient to be used as a guide for the installation of a percutaneous screw. Because the k-wire 1602 has been installed along the desired trajectory, a surgeon or other medical provider can proceed to install the percutaneous screw using the k-wire as a guide, so that the percutaneous screw will also follow the desired trajectory through the bone. Depending on the preference of the surgeon, the percutaneous screw can be installed before or after the cast is removed.

As used herein the directional terms, such as, but not limited to, "up" and "down", "upward" and "downward", "rear", "rearward" and "forward", "top" and "bottom", "inside" and "outer", "front" and "back", "inner" and "outer", "interior" and "exterior", "downward" and "upward", "horizontal" and "vertical" should be taken as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system.

It should be clear to one of ordinary skill that the foregoing provides a system and method for fixing a scaphoid or other fractured bone by inserting a k-wire through the fractured bone. The k-wire can be inserted through a guide block that can be held in place by a block holder that can be casted securely in place relative to the fractured bone. The guide block can be custom designed for each patient, and can be printed using a three-dimensional printer. The guide block that is secured in place relative to the fractured bone can ensure that the k-wire is inserted along a correct trajectory, so that the k-wire only needs to be inserted one time, thereby minimizing potential errors and complications.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, support frames can be various shapes and sizes, so that the present method can be applied to various other fractured bones that can benefit from correct placement of a k-wire. Likewise, a guide block can be custom designed for the installation of a k-wire through various bones that can benefit from correct installation of a k-wire. Also, as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Accordingly, this description is meant to be taken only by way of example, and not to otherwise limit the scope of this invention.

What is claimed is:
1. A guidance system comprising:
    a cast;
    a guide block, the guide block having a central lumen through the guide block along a predetermined k-wire trajectory; and a support frame, the support frame comprising at least one sidewall configured for holding the guide block, wherein the support frame is adapted to be held securely relative to a fractured bone of a patient by the cast, and the guide block is designed to fit within the support frame, so that the central lumen is aligned along the predetermined k-wire trajectory.

2. The guidance system of claim 1, wherein the support frame further comprises a brim.

3. The guidance system of claim 2, wherein the at least one sidewall defines a block chamber, the block chamber defining a first area near the brim that is smaller than a second area distant from the brim.

4. The guidance system of claim 1, further comprising a guide sleeve, the guide sleeve having a sleeve lumen that is aligned along the predetermined k-wire trajectory.

5. The guidance system of claim 1, wherein the guide block further comprises a frustum.

6. The guidance system of claim 1, wherein the k-wire trajectory defines a predetermined path adapted to pass through the fractured bone.

7. A guidance system comprising:
a cast configured to immobilize a portion of a patient;
a guide block defining a central lumen that defines a predetermined k-wire trajectory; and
a support frame secured relative to the portion of the patient by the cast, the support frame comprising at least one sidewall configured for receiving the guide block such that the central lumen is aligned along the predetermined k-wire trajectory.

8. The guidance system of claim 7, wherein the predetermined k-wire trajectory is determined based upon an image of the portion of the patient.

9. The guidance system of claim 8, wherein the image is captured after the cast and support frame are secured relative to the portion of the patient.

10. The guidance system of claim 8, wherein the image of the portion of the patient is acquired by a CT scan and is used to generate a 3D reconstruction of the portion of the patient.

11. The guidance system of claim 8, wherein the predetermined k-wire trajectory defines at least one of an entry point or an exit point relative to the 3D reconstruction.

12. The guidance system of claim 7, wherein the portion of the patient comprises a hand or a wrist.

* * * * *